US009464016B2

(12) United States Patent
Mollard et al.

(10) Patent No.: US 9,464,016 B2
(45) Date of Patent: Oct. 11, 2016

(54) CATECHOL DERIVATIVES FOR TREATMENT OF OXIDATIVE STRESS DISEASES

(75) Inventors: Paul Mollard, Saratoga, CA (US); Gloria Pfister, Mountain View, CA (US)

(73) Assignee: EDISON PHARMACEUTICALS, INC., Mountain View, CA (US)

( * ) Notice: Subject to any disclaimer, the term of this patent is extended or adjusted under 35 U.S.C. 154(b) by 65 days.

(21) Appl. No.: 14/124,671

(22) PCT Filed: Jun. 14, 2012

(86) PCT No.: PCT/US2012/042524
§ 371 (c)(1),
(2), (4) Date: Apr. 30, 2014

(87) PCT Pub. No.: WO2012/174286
PCT Pub. Date: Dec. 20, 2012

(65) Prior Publication Data
US 2014/0243424 A1    Aug. 28, 2014

Related U.S. Application Data

(60) Provisional application No. 61/520,750, filed on Jun. 14, 2011.

(51) Int. Cl.
C07C 39/19 (2006.01)
A61K 31/05 (2006.01)
A61K 31/122 (2006.01)
C07C 43/23 (2006.01)

(52) U.S. Cl.
CPC ............... C07C 39/19 (2013.01); A61K 31/05 (2013.01); A61K 31/122 (2013.01); C07C 43/23 (2013.01)

(58) Field of Classification Search
CPC .................................................... C07C 39/19
See application file for complete search history.

(56) References Cited

U.S. PATENT DOCUMENTS

| 6,133,322 | A | 10/2000 | Rustin et al. |
| 6,417,233 | B1 | 7/2002 | Sears et al. |
| 6,740,338 | B1 | 5/2004 | Chopra |
| 2002/0143049 | A1 | 10/2002 | Miller et al. |
| 2004/0105817 | A1 | 6/2004 | Gilat et al. |
| 2005/0065149 | A1 | 3/2005 | Wang et al. |
| 2006/0281809 | A1* | 12/2006 | Miller ............ A61K 31/355 514/458 |
| 2007/0072943 | A1 | 3/2007 | Miller et al. |
| 2007/0225261 | A1 | 9/2007 | Miller et al. |
| 2008/0152706 | A1 | 6/2008 | Shi et al. |
| 2009/0192179 | A1 | 7/2009 | Wang et al. |
| 2010/0063161 | A1 | 3/2010 | Miller et al. |
| 2010/0105930 | A1 | 4/2010 | Wesson et al. |
| 2010/0222436 | A1 | 9/2010 | Miller et al. |
| 2010/0273892 | A1 | 10/2010 | Miller et al. |
| 2010/0273894 | A1 | 10/2010 | Miller |
| 2011/0046156 | A1 | 2/2011 | Miller |
| 2011/0046219 | A1 | 2/2011 | Hinman et al. |
| 2011/0124679 | A1 | 5/2011 | Hinman et al. |
| 2011/0172312 | A1 | 7/2011 | Miller et al. |
| 2011/0207828 | A1 | 8/2011 | Miller et al. |
| 2011/0218208 | A1 | 9/2011 | Hinman et al. |
| 2011/0269776 | A1 | 11/2011 | Miller |
| 2012/0122934 | A1 | 5/2012 | Jankowski et al. |
| 2013/0109759 | A1 | 5/2013 | Miller |
| 2013/0267538 | A1 | 10/2013 | Walkinshaw et al. |
| 2013/0345312 | A1 | 12/2013 | Jankowski et al. |
| 2014/0031433 | A1 | 1/2014 | Miller et al. |
| 2014/0039065 | A1 | 2/2014 | Miller et al. |
| 2014/0243424 | A1 | 8/2014 | Mollard et al. |
| 2014/0249332 | A1 | 9/2014 | Mollard |
| 2014/0275045 | A1 | 9/2014 | Hinman et al. |
| 2014/0275054 | A1 | 9/2014 | Hinman et al. |
| 2015/0057363 | A1 | 2/2015 | Miller et al. |
| 2015/0216820 | A1 | 8/2015 | Miller et al. |
| 2015/0218079 | A1 | 8/2015 | Shrader et al. |
| 2015/0239818 | A1 | 8/2015 | Miller et al. |
| 2016/0024085 | A1 | 1/2016 | Hinman et al. |
| 2016/0039775 | A1 | 2/2016 | Hinman et al. |
| 2016/0039776 | A1 | 2/2016 | Hinman et al. |

FOREIGN PATENT DOCUMENTS

| WO | WO 00/23069 A1 | 4/2000 |
| WO | WO 2008143947 A1 * | 11/2008 |
| WO | WO 2010/126909 A1 | 11/2010 |
| WO | WO 2010/132440 A2 | 11/2010 |
| WO | WO 2014/194292 | 12/2014 |

OTHER PUBLICATIONS

Golub et al. Science, (1999), vol. 286, p. 531-537,@ p. 531.*
Cancer Research, (2006), vol. 66(7), p. 3351-3354.*
Schafer et al. Drug Discovery Today, 2008, 13 (21/22), 913-916.*
Horig et al. Journal of Translational Medicine 2004, 2(44), p. 1-8.*
International Search Report and Written Opinion in PCT/US2012/042524, mailed Sep. 4, 2012, 8 pages.
Extended European Search Report in EP application No. 12801330, mailed Oct. 28, 2014, 9 pages.
Pierrel et al. "Involvement of Mitochondrial Ferredoxin and Para-Aminobenzoic Acid in Yeast Coenzyme Q Biosynthesis," Chemistry & Biology, May 2010, vol. 17, No. 5, pp. 449-459, XP55146968.
Clarke, Catherine F. "New Advances in Coenzyme Q biosynthesis," Protoplasma, Sep. 2000, vol. 213, No. 3-4, pp. 134-147, XP55146971.
Poon et al. "Yeast and Rat Coq3 and Escherichia coli UbiG Polypeptides Catalyze Both O- Methyltransferase Steps in Coenzyme Q Biosynthesis," The Journal of Biological Chemistry, vol. 274, No. 31, Issue of Jul. 30, 1999, pp. 21665-21672.

(Continued)

Primary Examiner — Yong Chu
(74) Attorney, Agent, or Firm — Squire Patton Boggs (US) LLP

(57) ABSTRACT

Methods of treating or suppressing oxidative stress disorders affecting normal electron flow in the cells, including mitochondrial diseases, impaired energy processing disorders, neurodegenerative diseases, diseases of aging and diseases caused by reactive oxygen species are disclosed, as well as compounds useful in the methods of the invention, such as such as catechol or ortho-quinone derivatives of Formula (I).

10 Claims, No Drawings

(56) References Cited

OTHER PUBLICATIONS

Wheeler et al. "Density Functional Theory Analysis of Electronic Structure Variations across the Orthoquinone/Semiquinone/Catechol Redox Series," *J. Phys. Chemistry A*, 1999, vol. 103, pp. 4101-4112.

Hsu et al. "Complementation of *coq*3 Mutant Yeast by Mitochondrial Targeting of the *Escherichia coli* UbiG Polypeptide: Evidence That UbiG Catalyzes Both O-Methylation Steps in Ubiquinone Biosynthesis," *Biochemistry*, 1996, vol. 35, pp. 9797-9806.

Shepherd et al. "The Biosynthesis of Ubiquinone: Synthesis and Enzymatic Modification of Biosynthetic Precursors," *Tetrahedron Letters*, 1996, vol. 37, No. 14, pp. 2395-2398.

\* cited by examiner

CATECHOL DERIVATIVES FOR TREATMENT OF OXIDATIVE STRESS DISEASES

CROSS-REFERENCE TO RELATED APPLICATIONS

This patent application is a national phase application under 35 U.S.C. §371 of International Patent Application No. PCT/US2012/042524, filed on Jun. 14, 2012, which claims priority benefit of U.S. Provisional Patent Application No. 61/520,750, filed Jun. 14, 2011. The entire contents of those applications are hereby incorporated by reference herein.

TECHNICAL FIELD

The application discloses compositions and methods comprising 3- or 4-(ortho-hydroquinone)-derivatives (catechol derivatives) and 3- or 4-(ortho-quinonyl)-derivatives of Formula I as described herein, useful for treatment, prevention, or suppression of diseases, developmental delays and symptoms related to oxidative stress affecting normal electron flow in the cells. Examples of such diseases are mitochondrial disorders, impaired energy processing disorders, neurodegenerative diseases, diseases of aging and diseases caused by reactive oxygen species.

BACKGROUND

Oxidative stress is caused by disturbances to the normal redox state within cells. An imbalance between routine production and detoxification of reactive oxygen species such as peroxides and free radicals can result in oxidative damage to the cellular structure and machinery. The most important source of reactive oxygen species under normal conditions in aerobic organisms is probably the leakage of activated oxygen from mitochondria during normal oxidative respiration. Impairments associated with this process are suspected to contribute to mitochondrial disease, neurodegenerative disease, diseases of aging and diseases caused by reactive oxygen species.

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide ($NADH+H^+$) from oxidized nicotinamide adenine dinucleotide ($NAD^+$), and oxidative phosphorylation, during which $NADH+H^+$ is oxidized back to $NAD^+$. (The citric acid cycle also reduces flavin adenine dinucleotide, or FAD, to $FADH_2$; $FADH_2$ also participates in oxidative phosphorylation.)

The electrons released by oxidation of $NADH+H^+$ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Oxygen poisoning or toxicity is caused by high concentrations of oxygen that may be damaging to the body and increase the formation of free-radicals and other structures such as nitric oxide, peroxynitrite, and trioxidane. Normally, the body has many defense systems against such damage but at higher concentrations of free oxygen, these systems are eventually overwhelmed with time, and the rate of damage to cell membranes exceeds the capacity of systems which control or repair it. Cell damage and cell death then results.

Qualitative and/or quantitative disruptions in the transport of oxygen to tissues result in energy disruption in the function of red cells and contribute to various diseases such as haemoglobinopathies. Haemoglobinopathy is a kind of genetic defect that results in abnormal structure of one of the globin chains of the hemoglobin molecule. Common haemoglobinopathies include thalassemia and sickle-cell disease. Thalassemia is an inherited autosomal recessive blood disease. In thalassemia, the genetic defect results in reduced rate of synthesis of one of the globin chains that make up hemoglobin. While thalassemia is a quantitative problem of too few globins synthesized, sickle-cell disease is a qualitative problem of synthesis of an incorrectly functioning globin. Sickle-cell disease is a blood disorder characterized by red blood cells that assume an abnormal, rigid, sickle shape. Sickling decreases the cells' flexibility and results in their restricted movement through blood vessels, depriving downstream tissues of oxygen.

Another disorder caused by reactive oxygen species is Contrast Induced Nephropathy (CIN). Recent experimental data underlie the role of hypoxic tubular injury in the pathophysiology of radiocontrast nephropathy. Although systemic transient hypoxemia, increased blood viscosity, and a leftward shift of the oxygen-hemoglobin dissociation curve may all contribute to intrarenal hypoxia, imbalance between oxygen demand and supply plays a major role in radiocontrast-induced outer medullary hypoxic damage. Low oxygen tension normally exists in this renal region, reflecting the precarious regional oxygen supply and a high local metabolic rate and oxygen requirement, resulting from active salt reabsorption by medullary thick ascending limbs of Henle's loop. Radiologic contrast agents markedly aggravate outer medullary physiologic hypoxia. This results from enhanced metabolic activity and oxygen consumption (as a result of osmotic diuresis and increased salt delivery to the distal nephron) because the regional blood flow and the oxygen supply actually increase; (Heyman, S N et al, *Invest. Radio.* (1999), 34(11) 685-91 and Garfalo A S, *Ren. Fail.* (2007) 29 (2), 121-31.). Nephropathy induced by exposure to radiocontrast agents, is associated with significant in-hospital and long-term morbidity and mortality. Patients with preexisting renal failure are at particularly high risk. Contrast-Induced Nephropathy is a common clinical problem for which there is no effective therapy.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), Leigh disease, mitochondrial myopathy, encephalopathy, lactacidosis, and stroke (MELAS), Myoclonus Epilepsy Associated with Ragged-Red Fibers (MERRF) syndrome, and respiratory chain disorders. Some examples of diseases caused by deletions or mutations, such as in the "polymerase-gamma" gene which result in depletion of mitochondrial DNA, are Alper's disease and POLg-1 disease. Most mitochondrial diseases involve children who manifest the signs and symptoms of accelerated aging, including neurodegenerative diseases, stroke, blindness, hearing impairment, diabetes, and heart failure.

Friedreich's ataxia is an autosomal recessive neurodegenerative and cardiodegenerative disorder caused by decreased levels of the protein Frataxin. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Leber's Hereditary Optic Neuropathy (LHON) is a disease characterized by blindness which occurs on average between 27 and 34 years of age. Other symptoms may also occur, such as cardiac abnormalities and neurological complications.

Mitochondrial myopathy, encephalopathy, lactacidosis, and stroke (MELAS) can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke.

Myoclonus Epilepsy Associated with Ragged-Red Fibers (MERRF) syndrome is one of a group of rare muscular disorders that are called mitochondrial encephalomyopathies. Mitochondrial encephalomyopathies are disorders in which a defect in the genetic material arises from a part of the cell structure that releases energy (mitochondria). This can cause a dysfunction of the brain and muscles (encephalomyopathies). The mitochondrial defect as well as "ragged-red fibers" (an abnormality of tissue when viewed under a microscope) are always present. The most characteristic symptom of MERRF syndrome is myoclonic seizures that are usually sudden, brief, jerking, spasms that can affect the limbs or the entire body, difficulty speaking (dysarthria), optic atrophy, short stature, hearing loss, dementia, and involuntary jerking of the eyes (nystagmus) may also occur.

Leigh disease is a rare inherited neurometabolic disorder characterized by degeneration of the central nervous system where the symptoms usually begin between the ages of 3 months to 2 years and progress rapidly. In most children, the first signs may be poor sucking ability and loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function. Heart problems may also occur. The term "Leigh disease" includes Leigh-like syndromes and Leigh disease with one, or one or two, or more mutations in one or more than one genes selected from SURF-1, MTCO3, COX-10, COX-15, SCO2 and TACO1 genes. Children afflicted with Leigh disease with a SURF-1 mutation, typically die before the age of five years, often from respiratory failure.

Co-Enzyme Q10 Deficiency is a respiratory chain disorder, with syndromes such as myopathy with exercise intolerance and recurrent myoglobin in the urine manifested by ataxia, seizures or mental retardation and leading to renal failure (Di Mauro et al., (2005) *Neuromusc. Disord.*, 15:311-315), childhood-onset cerebellar ataxia and cerebellar atrophy (Masumeci et al., (2001) Neurology 56:849-855 and Lamperti et al., (2003) 60:1206:1208); and infantile encephalomyopathy associated with nephrosis. Biochemical measurement of muscle homogenates of patients with CoQ10 deficiency showed severely decreased activities of respiratory chain complexes I and II+III, while complex IV (COX) was moderately decreased (Gempel et al., (2007) *Brain,* 130(8):2037-2044).

Complex I Deficiency or NADH dehydrogenase NADH-CoQ reductase deficiency is a respiratory chain disorder, with symptoms classified by three major forms: (1) fatal infantile multisystem disorder, characterized by developmental delay, muscle weakness, heart disease, congenital lactic acidosis, and respiratory failure; (2) myopathy beginning in childhood or in adult life, manifesting as exercise intolerance or weakness; and (3) mitochondrial encephalomyopathy (including MELAS), which may begin in childhood or adult life and consists of variable combinations of symptoms and signs, including ophthalmoplegia, seizures, dementia, ataxia, hearing loss, pigmentary retinopathy, sensory neuropathy, and uncontrollable movements.

Complex II Deficiency or Succinate dehydrogenase deficiency is a respiratory chain disorder with symptoms including encephalomyopathy and various manifestations, including failure to thrive, developmental delay, hyoptonia, lethargy, respiratory failure, ataxia, myoclonus and lactic acidosis.

Complex III Deficiency or Ubiquinone-cytochrome C oxidoreductase deficiency is a respiratory chain disorder with symptoms categorized in four major forms: (1) fatal infantile encephalomyopathy, congenital lactic acidosis, hypotonia, dystrophic posturing, seizures, and coma; (2) encephalomyopathies of later onset (childhood to adult life): various combinations of weakness, short stature, ataxia, dementia, hearing loss, sensory neuropathy, pigmentary retinopathy, and pyramidal signs; (3) myopathy, with exercise intolerance evolving into fixed weakness; and (4) infantile histiocytoid cardiomyopathy.

Complex IV Deficiency or Cytochrome C oxidase deficiency is a respiratory chain disorder with symptoms categorized in two major forms: (1) encephalomyopathy, which is typically normal for the first 6 to 12 months of life and then show developmental regression, ataxia, lactic acidosis, optic atrophy, ophthalmoplegia, nystagmus, dystonia, pyramidal signs, respiratory problems and frequent seizures; and (2) myopathy with two main variants: (a) Fatal infantile myopathy—may begin soon after birth and accompanied by hypotonia, weakness, lactic acidosis, ragged-red fibers, respiratory failure, and kidney problems: and (b) Benign infantile myopathy—may begin soon after birth and accompanied by hypotonia, weakness, lactic acidosis, ragged-red fibers, respiratory problems, but (if the child survives) followed by spontaneous improvement.

Complex V Deficiency or ATP synthase deficiency is a respiratory chain disorder including symptoms such as slow, progressive myopathy.

CPEO or Chronic Progressive External Ophthalmoplegia Syndrome is a respiratory chain disorder including symptoms such as visual myopathy, retinitis pigmentosa, or dysfunction of the central nervous system.

Kearns-Sayre Syndrome (KSS) is a mitochondrial disease characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitoxic, neuronal injury, such as that associated with cerebral vascular accidents, seizures and ischemia.

The diseases above appear to be caused by defects in Complex I of the respiratory chain. Electron transfer from Complex I to the remainder of the respiratory chain is mediated by the compound coenzyme Q (also known as Ubiquinone). Oxidized coenzyme Q ($CoQ^{ox}$ or Ubiquinone) is reduced by Complex I to reduced coenzyme Q ($CoQ^{red}$ or Ubiquinol). The reduced coenzyme Q then transfers its electrons to Complex III of the respiratory chain (skipping over complex II), where it is re-oxidized to $CoQ^{ox}$ (Ubiquinone). $CoQ^{ox}$ can then participate in further iterations of electron transfer.

Very few treatments are available for patients suffering from these mitochondrial diseases. Recently, the compound Idebenone has been proposed for treatment of Friedreich's ataxia. While the clinical effects of Idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. Administration of coenzyme Q10 (CoQ10) and vitamin supplements has shown only transient beneficial effects in individual cases of KSS. CoQ10 supplementation has also been used for the treatment of CoQ10 deficiency with mixed results.

Oxidative stress is suspected to be important in neurodegenerative diseases such as Motor Neuron Disease, Amyotrophic Lateral Sclerosis (ALS), Creutzfeldt-Jakob disease, Machado-Joseph disease, Spino-cerebellar ataxia, Multiple sclerosis (MS), Parkinson's disease, Alzheimer's disease, and Huntington's disease. Oxidative stress is thought to be linked to certain cardiovascular disease and also plays a role in the ischemic cascade due to oxygen reperfusion injury following hypoxia. This cascade includes both strokes and heart attacks.

Damage accumulation theory, also known as the free radical theory of aging, invokes random effects of free radicals produced during aerobic metabolism that cause damage to DNA, lipids and proteins and accumulate over time. The concept of free radicals playing a role in the aging process was first introduced by Himan D (1956), Aging—A theory based on free-radical and radiation chemistry *J. Gerontol.* 11, 298-300.

According to the free radical theory of aging, the process of aging begins with oxygen metabolism (Valko et al, (2004) Role of oxygen radicals in DNA damage and cancer incidence, *Mol. Cell. Biochem.*, 266, 37-56). Even under ideal conditions some electrons "leak" from the electron transport chain. These leaking electrons interact with oxygen to produce superoxide radicals, so that under physiological conditions, about 1-3% of the oxygen molecules in the mitochondria are converted into superoxide. The primary site of radical oxygen damage from superoxide radical is mitochondrial DNA (mtDNA) (Cadenas et al., (2000) Mitochondrial free radical generation, oxidative stress and aging, *Free Radic. Res,* 28, 601-609). The cell repairs much of the damage done to nuclear DNA (nDNA) but mtDNA cannot be fixed. Therefore, extensive mtDNA dmage accumulates over time and shuts down mitochondria causing cells to die and organism to age.

Some of the diseases associated with increasing age are cancer, diabetes mellitus, hypertension, atherosclerosis, ischemia/reperfusion injury, rheumatoid arthritis, neurodegenerative disorders such as dementia, Alzheimer's and Parkinson's. Diseases resulting from the process of aging as a physiological decline include decreases in muscle strength, cardiopulmonary function, vision and hearing as well as wrinkled skin and graying hair.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitoxic, neuronal injury, cerebral vascular accidents such as that associated with seizures, stroke and ischemia.

Recently, Hayashi et al, (Science, published online 3 Apr. 2008: 10.1126/science. 1156906) indicated that mitochondrial DNA mutations can contribute to tumor progression by enhancing the metastatic potential of tumor cells.

Other recent studies have suggested that as many 20 percent of patients with pervasive development disorders such as autism have markers for mitochondrial disease, (Shoffner, J. the 60th Annual American Academy of Neurology meeting in Chicago, Apr. 12-19, 2008; Poling, J S et al *J. child Neurol.* 2008, 21(2) 170-2; and Rossignol et al., *Am. J. Biochem. & Biotech.* (2008)$_4$, 208-217.) Some cases of autism have been associated with bioenergetic metabolism deficiency suggested by the detection of high lactate levels in some patients (Coleman M. et al, Autism and Lactic Acidosis, *J. Autism Dev Disord.*, (1985) 15: 1-8; Laszlo et al Serum serotonin, lactate and pyruvate levels in infantile autistic children, *Clin. Chim. Acta* (1994) 229:205-207; and Chugani et al., Evidence of altered energy metabolism in autistic children, *Progr. Neuropsychopharmacol Biol Psychiat.*, (1999) 23:635-641) and by nuclear magnetic resonance imagining as well as positron emission tomography scanning which documented abnormalities in brain metabolism.

Genetic mitochondrial mutations have also been correlated to hearing loss. This has been demonstrated by the presence of mitochondrial DNA mutations in families with non-syndromic progressive sensorineural hearing loss (SNHL) (Berretinin, S. et al., *Biosci. Rep.* (2008) 28. 45-59 and Guan M, et al, *Human Mol Gen* 2000, 9, 12, 1787-93). Involvement of mitochondrial pathways in cisplatin-induced apoptosis in a model in vitro system of cultured auditory cells is suggested by Devarjan et al. (*Hearing Research*, (2002) 174, 45-54). Involvement of the mitochondrial permeability transition in gentamicin-induced apoptosis is suggested by Dehne et al., (*Hearing Research* (2002) 169. 47-55).

The diseases above appear to be caused by defects in complex I of the respiratory chain. Electron transfer from complex I to the remainder of the respiratory chain is mediated by the compound coenzyme Q (also known as ubiquinone). Oxidized coenzyme Q ($CoQ^{ox}$ or ubiquinone) is reduced by complex I to reduced coenzyme Q ($CoQ^{red}$ or ubiquinol). The reduced coenzyme Q then transfers its electrons to complex III of the respiratory chain (skipping over complex II), where it is re-oxidized to $Coq^{ox}$ (ubiquinone). $CoQ^{ox}$ can then participate in further iterations of electron transfer.

Very few treatments are available for patients suffering from these diseases. Recently, the compound idebenone has been proposed for treatment of Friedreich's ataxia. While the clinical effects of idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. Administration of coenzyme Q10 (CoQ10) and vitamin supplements have shown only transient beneficial effects in individual cases of KSS. Another compound, Tocotrienol quinone has been proposed for treating mitochondrial disorders (see e.g. U.S. application Ser. No. 12/777,179, U.S. application Ser. No. 12/982,716, U.S. application Ser. No. 12/768,554; U.S. application Ser. No. 12/768,565).

Hydroxytyrosol has been described for its benefits increasing mitochondria biogenesis (U.S. application Ser. No. 12/988,090), for the treatment of vision disorders (WO 2008/128552); for the treatment of ischemic heart diseases and inflammation (U.S. Pat. No. 4,618,627) and its protection against oxidative damage (Zhu, L et al. *Journal of Nutritional Biochemistry* 2010, 21(11):1089-98.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

DISCLOSURE OF THE INVENTION

In one embodiment, the invention embraces catechol derivatives and their oxidized forms with structures of formula I:

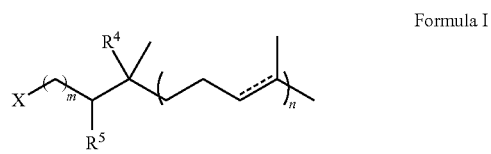

Formula I where X is selected from the group consisting of:

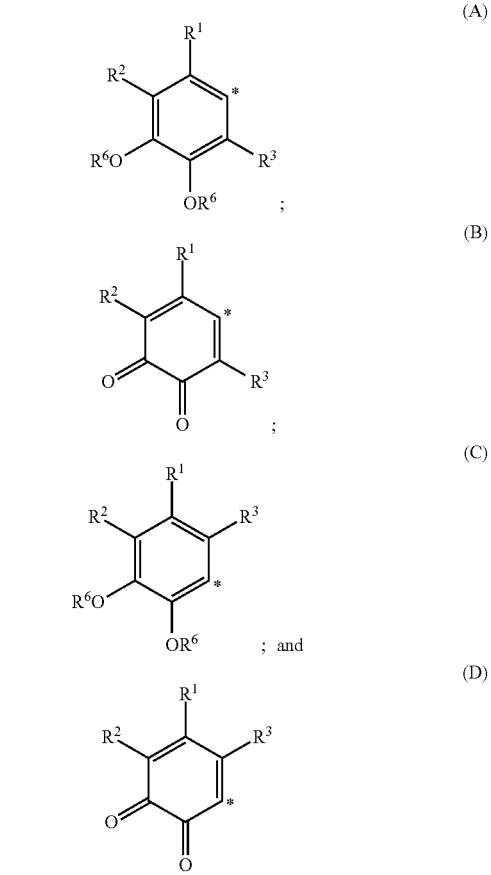

where the * indicates the point of attachment of X to the rest of the molecule; the bond indicated by a dashed line can be double or single;

m is 0 or 1;

n is 1 to 10;

$R^1$, $R^2$ and $R^3$ are independently selected from hydrogen, $C_1$-$C_6$-alkyl, $C_1$-$C_6$-haloalkyl, and halogen;

$R^4$ is OH and $R^5$ is hydrogen; or $R^4$ and $R^5$ are both hydrogen; or $R^4$ and $R^5$ together with the atoms to which they are attached form a double bond; and $R^6$ is hydrogen, $C_1$-$C_6$-alkyl, —C(O)$C_1$-$C_6$-alkyl or —C(O)aryl;

or all salts, stereoisomers, mixtures of stereoisomers, prodrugs, metabolites, solvates, or hydrates thereof.

In some embodiments, the invention embraces compounds of Formula I wherein $R^6$ is hydrogen. In other embodiments, the invention embraces compounds of Formula I wherein $R^6$ is $C_1$-$C_6$-alkyl. In other embodiments, the invention embraces compounds of Formula I wherein $R^6$ is —C(O)$C_1$-$C_6$-alkyl. In other embodiments, the invention embraces compounds of Formula I wherein $R^6$ is —C(O)aryl.

In some embodiments, the invention embraces compounds of Formula I wherein X is (A). In other embodiments, the invention embraces compounds of Formula I wherein X is (B). In other embodiments, the invention embraces compounds of Formula I wherein X is (C). In other embodiments, the invention embraces compounds of Formula I wherein X is (D).

In some embodiments, the invention embraces compounds of Formula I, wherein $R^4$ is OH and $R^5$ is hydrogen. In other embodiments, the invention embraces compounds of Formula I, wherein $R^4$ and $R^5$ are both hydrogen. In other embodiments, the invention embraces compounds of Formula I, wherein $R^4$ and $R^5$ together with the atoms to which they are attached form a double bond.

In some embodiments, the invention embraces compounds of Formula I, wherein m is 0. In other embodiments, the invention embraces compounds of Formula I, wherein m is 1. In some embodiments, the invention embraces compounds of Formula I, wherein n is 1 to 10. In other embodiments, the invention embraces compounds of Formula I, wherein n is 1 to 6. In other embodiments, the invention embraces compounds of Formula I, wherein n is 1 to 4.

In one embodiment, the invention embraces catechol derivatives of Formula Ia:

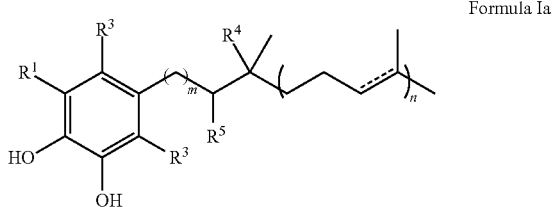

Formula Ia where,
the bond indicated by a dashed line can be double or single;
m is 0 or 1
n is 1 to 4;
$R^1$, $R^2$ and $R^3$ are independently selected from hydrogen, $C_1$-$C_6$-alkyl, $C_1$-$C_6$-haloalkyl and halogen;
$R^4$ is OH and $R^5$ is hydrogen; or $R^4$ and $R^5$ are both hydrogen; or $R^4$ and $R^5$ together with the atoms to which they are attached form a double bond;
or all salts, stereoisomers, mixtures of stereoisomers, prodrugs, metabolites, solvates, or hydrates thereof.

In some embodiments, the invention embraces compounds of Formula Ia, wherein $R^1$, $R^2$ and $R^3$ are independently selected from hydrogen and $C_1$-$C_6$-alkyl. In other embodiments, the invention embraces compounds of Formula Ia, wherein $R^1$, $R^2$ and $R^3$ are hydrogen. In some embodiments, the invention embraces compounds of Formula Ia, wherein $R^1$, $R^2$ and $R^3$ are independently selected from $C_1$-$C_6$-alkyl. In some embodiments, the invention embraces compounds of Formula Ia, wherein one of $R^1$, $R^2$ and $R^3$ is $C_1$-$C_6$-alkyl, and the others are hydrogen. In some embodiments, the invention embraces compounds of Formula Ia, wherein two of $R^1$, $R^2$ and $R^3$ are $C_1$-$C_6$-alkyl and the others are hydrogen. In some embodiments, the invention embraces compounds of Formula Ia, wherein one of $R^1$, $R^2$ and $R^3$ is halogen. In some embodiments, the invention embraces compounds of Formula Ia, wherein two of $R^1$, $R^2$ and $R^3$ are halogen. In some embodiments, the invention embraces compounds of Formula Ia, wherein one of $R^1$, $R^2$ and $R^3$ is $C_1$-$C_6$-haloalkyl. In some embodiments, the invention embraces compounds of Formula Ia, wherein two of $R^1$, $R^2$ and $R^3$ are $C_1$-$C_6$-haloalkyl.

In some embodiments, the invention embraces compounds of Formula Ia, wherein $R^4$ is OH and $R^5$ is hydrogen. In some embodiments, where $R^4$ is OH, $R^4$ has an (R) configuration. In some embodiments, where $R^4$ is OH, $R^4$ has an (S) configuration. In some embodiments the invention embraces compounds of Formula Ia, wherein $R^4$ and $R^5$ are both hydrogen. In some embodiments, the invention embraces compounds of Formula Ia, wherein $R^4$ and $R^5$ together with the atoms to which they are attached form a double bond.

In some embodiments, the invention embraces compounds of Formula Ia, wherein m is 0. In other embodiments, the invention embraces compounds of Formula Ia, wherein m is 1.

In some embodiments, the invention embraces compounds of Formula Ia, wherein n is 1. In some embodiments, the invention embraces compounds of Formula Ia, wherein n is 2. In some embodiments, the invention embraces compounds of Formula Ia, wherein n is 3. In some embodiments, the invention embraces compounds of Formula Ia, wherein n is 4.

In some embodiments, the invention embraces compounds of Formula Ia, wherein the bond indicated by a dashed line is in every occurrence a double bond. In some embodiments, the invention embraces compounds of Formula Ia, wherein the bond indicated by a dashed line is not in every occurrence a double bond. In some embodiments, the invention embraces compounds of Formula Ia, wherein the bond indicated by a dashed line is in every occurrence a single bond. In some embodiments, the invention embraces compounds of Formula Ia, wherein the bond indicated by a dashed line is not in every occurrence a single bond.

In some embodiments, the invention embraces compounds of Formula Ia, wherein the bond indicated by a dashed line is in every occurrence a double bond and n is 3. In some embodiments, the invention embraces compounds of Formula Ia, wherein the bond indicated by a dashed line is in every occurrence a single bond and n is 3.

In some embodiments, the invention embraces compounds of Formula Ia, wherein the bond indicated by a dashed line is in every occurrence a double bond, n is 3, $R^4$ is OH and $R^5$ is hydrogen. In other embodiments, the invention embraces compounds of Formula Ia, wherein the bond indicated by a dashed line is in every occurrence a double bond, n is 3 and $R^4$ and $R^5$ together with the atoms to which they are attached form a double bond. In other embodiments, the invention embraces compounds of Formula Ia, wherein the bond indicated by a dashed line is in every occurrence a double bond, n is 3 and $R^4$ and $R^5$ are hydrogen.

In some embodiments, the invention embraces compounds of Formula Ia, wherein the bond indicated by a dashed line is in every occurrence a double bond, n is 3, m is 0, $R^4$ is OH and $R^5$ is hydrogen. In some embodiments, the invention embraces compounds of Formula Ia, wherein the bond indicated by a dashed line is in every occurrence a double bond, n is 3, m is 1, $R^4$ is OH and $R^5$ is hydrogen. In some embodiments, the invention embraces compounds of Formula Ia, wherein the bond indicated by a dashed line is in every occurrence a double bond, n is 3, m is 0 and $R^4$ and $R^5$ together with the atoms to which they are attached form a double bond. In some embodiments, the invention embraces compounds of Formula Ia, wherein the bond indicated by a dashed line is in every occurrence a double bond, n is 3, m is 1 and $R^4$ and $R^5$ together with the atoms to which they are attached form a double bond. In some embodiments, the invention embraces compounds of Formula Ia, wherein the bond indicated by a dashed line is in every occurrence a double bond, n is 3, m is O and $R^4$ and $R^5$ are hydrogen. In some embodiments, the invention embraces compounds of Formula Ia, wherein the bond indicated by a dashed line is in every occurrence a double bond, n is 3, m is 1 and $R^4$ and $R^5$ are hydrogen, In some embodiments, the invention embraces compounds of Formula Ia, wherein the bond indicated by a dashed line is in every occurrence a single bond, n is 3, $R^4$ is OH and $R^5$ is hydrogen. In some embodiments, the invention embraces compounds of Formula Ia, wherein the bond indicated by a dashed line is in every occurrence a single bond, n is 3, and $R^4$ and $R^5$ are hydrogen.

In some embodiments, the invention embraces compounds of Formula Ia, wherein the bond indicated by a dashed line is in every occurrence a single bond, n is 3, m is 0, $R^4$ is OH and $R^5$ is hydrogen. In some embodiments, the invention embraces compounds of Formula Ia, wherein the bond indicated by a dashed line is in every occurrence a single bond, n is 3, m is 1, $R^4$ is OH and $R^5$ is hydrogen. In some embodiments, the invention embraces compounds of Formula Ia, wherein the bond indicated by a dashed line is in every occurrence a single bond, n is 3, m is 0, and $R^4$ and $R^5$ are hydrogen. In some embodiments, the invention embraces compounds of Formula Ia, wherein the bond indicated by a dashed line is in every occurrence a single bond, n is 3, m is 1, and $R^4$ and $R^5$ are hydrogen.

In some embodiments, the compound is selected from:
4-(3-hydroxy-3,7,11,15-tetramethylhexadeca-6,10,14-trien-1-yl)benzene-1,2-diol;
4-(3-hydroxy-3,7,11,15,19-pentamethylicosa-6,10,14,18-tetraen-1-yl)benzene-1,2-diol;
4-(3-hydroxy-3,7,11-trimethyldodeca-6,10-dien-1-yl)benzene-1,2-diol;
4-(3-hydroxy-3,7-dimethyloct-6-en-1-yl)benzene-1,2-diol;
4-(3-hydroxy-3,7,11,15-tetramethylhexadeca-6,10,14-trien-1-yl)-3,5,6-trimethylbenzene-1,2-diol;
4-(3-hydroxy-3,7,11,15-tetramethylhexadeca-6,10,14-trien-1-yl)-3,5-dimethylbenzene-1,2-diol;
5-(3-hydroxy-3,7,11,15-tetramethylhexadeca-6,10,14-trien-1-yl)-3,4-dimethylbenzene-1,2-diol;
4-(3-hydroxy-3,7,11,15-tetramethylhexadeca-6,10,14-trien-1-yl)-3,6-dimethylbenzene-1,2-diol;
5-(3-hydroxy-3,7,11,15-tetramethylhexadeca-6,10,14-trien-1-yl)-3-methylbenzene-1,2-diol;
4-(3-hydroxy-3,7,11,15-tetramethylhexadeca-6,10,14-trien-1-yl)-5-methylbenzene-1,2-diol;
4-(3-hydroxy-3,7,11,15-tetramethylhexadeca-6,10,14-trien-1-yl)-3-methylbenzene-1,2-diol;
4-(3-hydroxy-3,7,11,15-tetramethylhexadecyl)benzene-1,2-diol;
4-(3-hydroxy-3,7,11,15-tetramethylhexadecyl)-3,5,6-trimethylbenzene-1,2-diol;
4-(3-hydroxy-3,7,11,15-tetramethylhexadecyl)-3,5-dimethylbenzene-1,2-diol;
5-(3-hydroxy-3,7,11,15-tetramethylhexadecyl)-3,4-dimethylbenzene-1,2-diol;
4-(3-hydroxy-3,7,11,15-tetramethylhexadecyl)-3,6-dimethylbenzene-1,2-diol;
5-(3-hydroxy-3,7,11,15-tetramethylhexadecyl)-3-methylbenzene-1,2-diol;
4-(3-hydroxy-3,7,11,15-tetramethylhexadecyl)-5-methylbenzene-1,2-diol;
4-(3-hydroxy-3,7,11,15-tetramethylhexadecyl)-3-methylbenzene-1,2-diol;
4-(3,7,11,15-tetramethylhexadeca-2,6,10,14-tetraen-1-yl)benzene-1,2-diol;
4-(3,7,11-trimethyldodeca-2,6,10-trien-1-yl)benzene-1,2-diol;
4-(3,7-dimethylocta-2,6-dien-1-yl)benzene-1,2-diol;
3,4,6-trimethyl-5-(3,7,11,15-tetramethylhexadeca-2,6,10,14-tetraen-1-yl)benzene-1,2-diol;
3,4-dimethyl-5-(3,7,11,15-tetramethylhexadeca-2,6,10,14-tetraen-1-yl)benzene-1,2-diol;
3,6-dimethyl-4-(3,7,11,15-tetramethylhexadeca-2,6,10,14-tetraen-1-yl)benzene-1,2-diol;
3-methyl-5-(3,7,11,15-tetramethylhexadeca-2,6,10,14-tetraen-1-yl)benzene-1,2-diol;
4-methyl-5-(3,7,11,15-tetramethylhexadeca-2,6,10,14-tetraen-1-yl)benzene-1,2-diol;
3-methyl-4-(3,7,11,15-tetramethylhexadeca-2,6,10,14-tetraen-1-yl)benzene-1,2-diol;
4-(3,7,11,15-tetramethylhexadecyl)benzene-1,2-diol;
3,4,6-trimethyl-5-(3,7,11,15-tetramethylhexadecyl)benzene-1,2-diol;
3,4-dimethyl-5-(3,7,11,15-tetramethylhexadecyl)benzene-1,2-diol;
3,6-dimethyl-4-(3,7,11,15-tetramethylhexadecyl)benzene-1,2-diol;
3,5-dimethyl-4-(3,7,11,15-tetramethylhexadecyl)benzene-1,2-diol;
4-methyl-5-(3,7,11,15-tetramethylhexadecyl)benzene-1,2-diol;
3-methyl-5-(3,7,11,15-tetramethylhexadecyl)benzene-1,2-diol; and
3-methyl-4-(3,7,11,15-tetramethylhexadecyl)benzene-1,2-diol;

or all salts, stereoisomers, mixtures of stereoisomers, prodrugs, metabolites, solvates, or hydrates thereof.

In other embodiments, the compounds are selected from 4-((6E,10E)-3-hydroxy-3,7,11,15-tetramethylhexadeca-6,10,14-trien-1-yl)benzene-1,2-diol and 4-((2E,6E,10E)-3,7,11,15-tetramethylhexadeca-2,6,10,14-tetraen-1-yl)benzene-1,2-diol.

In one embodiment, the invention embraces catechol derivatives of Formula Ib:

Formula Ib

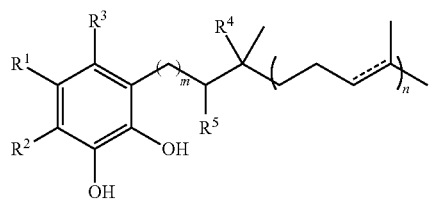

where,
the bond indicated by a dashed line can be double or single;
m is 0 or 1
n is 1 to 4;
$R^1$, $R^2$ and $R^3$ are independently selected from hydrogen, $C_1$-$C_6$-alkyl, $C_1$-$C_6$-haloalkyl, and halogen;
$R^4$ is OH and $R^5$ is hydrogen; or $R^4$ and $R^5$ are both hydrogen; or $R^4$ and $R^5$ together with the atoms to which they are attached form a double bond;
or all salts, stereoisomers, mixtures of stereoisomers, prodrugs, metabolites, solvates, or hydrates thereof.

In some embodiments, the invention embraces compounds of Formula Ib, wherein $R^1$, $R^2$ and $R^3$ are independently selected from hydrogen and $C_1$-$C_6$-alkyl. In other embodiments, the invention embraces compounds of Formula Ib, wherein $R^1$, $R^2$ and $R^3$ are hydrogen. In some embodiments, the invention embraces compounds of Formula Ib, wherein $R^1$, $R^2$ and $R^3$ are independently selected from $C_1$-$C_6$-alkyl. In some embodiments, the invention embraces compounds of Formula Ib, wherein one of $R^1$, $R^2$ and $R^3$ is $C_1$-$C_6$-alkyl, and the others are hydrogen. In some embodiments, the invention embraces compounds of Formula Ib, wherein two of $R^1$, $R^2$ and $R^3$ are $C_1$-$C_6$-alkyl and the others are hydrogen. In some embodiments, the invention embraces compounds of Formula Ib, wherein one of $R^1$, $R^2$ and $R^3$ is halogen. In some embodiments, the invention embraces compounds of Formula Ib, wherein two of $R^1$, $R^2$ and $R^3$ are halogen. In some embodiments, the invention embraces compounds of Formula Ib, wherein one of $R^1$, $R^2$ and $R^3$ is $C_1$-$C_6$-haloalkyl. In some embodiments, the invention embraces compounds of Formula Ib, wherein two of $R^1$, $R^2$ and $R^3$ are $C_1$-$C_6$-haloalkyl.

In some embodiments the invention embraces compounds of Formula Ib, wherein $R^4$ is OH and $R^5$ is hydrogen. In some embodiments, where $R^4$ is OH, $R^4$ has an (R) configuration. In some embodiments, where $R^4$ is OH, $R^4$ has an (S) configuration. In some embodiments the invention embraces compounds of Formula Ib, wherein $R^4$ and $R^5$ are both hydrogen. In some embodiments the invention embraces compounds of Formula Ib, wherein $R^4$ and $R^5$ together with the atoms to which they are attached form a double bond.

In some embodiments, the invention embraces compounds of Formula Ib, wherein m is 0. In other embodiments, the invention embraces compounds of Formula Ib, wherein m is 1.

In some embodiments, the invention embraces compounds of Formula Ib, wherein n is 1. In some embodiments, the invention embraces compounds of Formula Ib, wherein n is 2. In some embodiments, the invention embraces compounds of Formula Ib, wherein n is 3. In some embodiments, the invention embraces compounds of Formula Ib, wherein n is 4.

In some embodiments, the invention embraces compounds of Formula Ib, wherein the bond indicated by a dashed line is in every occurrence a double bond. In other embodiments, the invention embraces compounds of Formula Ib, wherein the bond indicated by a dashed line is not in every occurrence a double bond. In some embodiments, the invention embraces compounds of Formula Ib, wherein the bond indicated by a dashed line is in every occurrence a single bond. In other embodiments, the invention embraces compounds of Formula Ib, wherein the bond indicated by a dashed line is not in every occurrence a single bond.

In some embodiments, the invention embraces compounds of Formula Ib, wherein the bond indicated by a dashed line is in every occurrence a double bond and n is 3.

In some embodiments, the invention embraces compounds of Formula Ib, wherein the bond indicated by a dashed line is in every occurrence a single bond and n is 3.

In some embodiments, the invention embraces compounds of Formula Ib, wherein the bond indicated by a dashed line is in every occurrence a double bond, n is 3, $R^4$ is OH and $R^5$ is hydrogen. In other embodiments, the invention embraces compounds of Formula Ib, wherein the bond indicated by a dashed line is in every occurrence a double bond, n is 3 and $R^4$ and $R^5$ together with the atoms to which they are attached form a double bond. In other embodiments, the invention embraces compounds of Formula Ib, wherein the bond indicated by a dashed line is in every occurrence a double bond, n is 3 and $R^4$ and $R^5$ are hydrogen.

In some embodiments, the invention embraces compounds of Formula Ib, wherein the bond indicated by a dashed line is in every occurrence a double bond, n is 3, m is 0, $R^4$ is OH and $R^5$ is hydrogen. In some embodiments, the invention embraces compounds of Formula Ib, wherein the bond indicated by a dashed line is in every occurrence a double bond, n is 3, m is 1, $R^4$ is OH and $R^5$ is hydrogen. In some embodiments, the invention embraces compounds of Formula Ib, wherein the bond indicated by a dashed line is in every occurrence a double bond, n is 3, m is 0 and $R^4$ and $R^5$ together with the atoms to which they are attached form a double bond. In some embodiments, the invention embraces compounds of Formula Ib, wherein the bond indicated by a dashed line is in every occurrence a double bond, n is 3, m is 1 and $R^4$ and $R^5$ together with the atoms to which they are attached form a double bond. In some embodiments, the invention embraces compounds of Formula Ib, wherein the bond indicated by a dashed line is in every occurrence a double bond, n is 3, m is O and $R^4$ and $R^5$ are hydrogen. In some embodiments, the invention embraces compounds of Formula Ib, wherein the bond indicated by a dashed line is in every occurrence a double bond, n is 3, m is 1 and $R^4$ and $R^5$ are hydrogen.

In some embodiments, the invention embraces compounds of Formula Ib, wherein the bond indicated by a dashed line is in every occurrence a single bond, n is 3, $R^4$ is OH and $R^5$ is hydrogen. In some embodiments, the invention embraces compounds of Formula Ib, wherein the bond indicated by a dashed line is in every occurrence a single bond, n is 3, and $R^4$ and $R^5$ are hydrogen.

In some embodiments, the invention embraces compounds of Formula Ib, wherein the bond indicated by a dashed line is in every occurrence a single bond, n is 3, m is 0, $R^4$ is OH and $R^5$ is hydrogen. In some embodiments, the invention embraces compounds of Formula Ib, wherein the bond indicated by a dashed line is in every occurrence a single bond, n is 3, m is 1, $R^4$ is OH and $R^5$ is hydrogen. In some embodiments, the invention embraces compounds of Formula Ib, wherein the bond indicated by a dashed line is in every occurrence a single bond, n is 3, m is 0, and $R^4$ and $R^5$ are hydrogen. In some embodiments, the invention embraces compounds of Formula Ib, wherein the bond indicated by a dashed line is in every occurrence a single bond, n is 3, m is 1, and $R^4$ and $R^5$ are hydrogen.

In some embodiments, the compound is selected from:
3-(3-hydroxy-3,7,11,15-tetramethylhexadeca-6,10,14-trien-1-yl)benzene-1,2-diol;
3-(3-hydroxy-3,7,11,15-tetramethylhexadeca-6,10,14-trien-1-yl)-4,5,6-trimethylbenzene-1,2-diol;
6-(3-hydroxy-3,7,11,15-tetramethylhexadeca-6,10,14-trien-1-yl)-3,4-dimethylbenzene-1,2-diol;

3-(3-hydroxy-3,7,11,15-tetramethylhexadeca-6,10,14-trien-1-yl)-4,5-dimethylbenzene-1,2-diol;
3-(3-hydroxy-3,7,11,15-tetramethylhexadeca-6,10,14-trien-1-yl)-4,6-dimethylbenzene-1,2-diol;
3-(3-hydroxy-3,7,11,15-tetramethylhexadeca-6,10,14-trien-1-yl)-4-methylbenzene-1,2-diol;
3-(3-hydroxy-3,7,11,15-tetramethylhexadeca-6,10,14-trien-1-yl)-5-methylbenzene-1,2-diol;
3-(3-hydroxy-3,7,11,15-tetramethylhexadeca-6,10,14-trien-1-yl)-6-methylbenzene-1,2-diol;
3-(3-hydroxy-3,7,11,15,19-pentamethylicosa-6,10,14,18-tetraen-1-yl)benzene-1,2-diol;
3-(3-hydroxy-3,7,11-trimethyldodeca-6,10-dien-1-yl)benzene-1,2-diol;
3-(3-hydroxy-3,7-dimethyloct-6-en-1-yl)benzene-1,2-diol;
3-(3,7,11,15-tetramethylhexadeca-2,6,10,14-tetraen-1-yl)benzene-1,2-diol;
3-(3,7,11-trimethyldodeca-2,6,10-trien-1-yl)benzene-1,2-diol;
3,4,5-trimethyl-6-(3,7,11-trimethyldodeca-2,6,10-trien-1-yl)benzene-1,2-diol;
4,5-dimethyl-3-(3,7,11-trimethyldodeca-2,6,10-trien-1-yl)benzene-1,2-diol;
3,4-dimethyl-6-(3,7,11-trimethyldodeca-2,6,10-trien-1-yl)benzene-1,2-diol;
4,6-dimethyl-3-(3,7,11-trimethyldodeca-2,6,10-trien-1-yl)benzene-1,2-diol;
4-methyl-3-(3,7,11-trimethyldodeca-2,6,10-trien-1-yl)benzene-1,2-diol;
5-methyl-3-(3,7,11-trimethyldodeca-2,6,10-trien-1-yl)benzene-1,2-diol; and
3-methyl-6-(3,7,11-trimethyldodeca-2,6,10-trien-1-yl)benzene-1,2-diol;
or all salts, stereoisomers, mixtures of stereoisomers, prodrugs, metabolites, solvates, or hydrates thereof.

In other embodiments, the compound is selected from 3-((6E,10E)-3-hydroxy-3,7,11,15-tetramethylhexadeca-6,10,14-trien-1-yl)benzene-1,2-diol and 3-((2E,6E,10E)-3,7,11,15-tetramethylhexadeca-2,6,10,14-tetraen-1-yl)benzene-1,2-diol.

In another embodiment, the invention embraces one or more compounds of Formula I, Ia and/or Ib, in combination with a pharmaceutically acceptable excipient, carrier or vehicle.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of Formula I, or all salts, stereoisomers, mixtures of stereoisomers, prodrugs, metabolites, solvates, or hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of Formula Ia, or all salts, stereoisomers, mixtures of stereoisomers, prodrugs, metabolites, solvates, or hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of Formula Ib, or all salts, stereoisomers, mixtures of stereoisomers, prodrugs, metabolites, solvates, or hydrates thereof.

In other embodiments, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, and Stroke (MELAS); Leber's Hereditary Optic Neuropathy (LHON); Leigh Disease; Kearns-Sayre Syndrome (KSS); Friedreich's Ataxia (FRDA); other myopathies; CoQ10 deficiency, cardiomyopathy; encephalomyopathy; renal tubular acidosis; neurodegenerative diseases; Parkinson's Disease; Alzheimer's Disease; Amyotrophic Lateral Sclerosis (ALS); motor neuron diseases; other neurological diseases; epilepsy; genetic diseases; Huntington's Disease; mood disorders; schizophrenia; bipolar disorder; age-associated diseases; cerebral vascular accidents, macular degeneration; diabetes; and cancer.

In another embodiment, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, and Stroke (MELAS); Leber's Hereditary Optic Neuropathy (LHON); Leigh Disease; Kearns-Sayre Syndrome (KSS); Friedreich's Ataxia (FRDA) and CoQ10 deficiency.

In another embodiment, including any of the foregoing embodiments the disorder is selected from hearing impairment and pervasive development disorders selected from Autistic Disorder, Asperger's Disorder, Childhood Disintegrative Disorder (CDD), Rett's Disorder, and PDD-Not Otherwise Specified (PDD-NOS).

In another embodiment of the invention, including any of the foregoing embodiments, the mitochondrial disorder is Friedreich's Ataxia (FRDA). In another embodiment of the invention, the mitochondrial disorder is Leber's Hereditary Optic Neuropathy (LHON). In another embodiment of the invention, including any of the foregoing embodiments, the mitochondrial disorder is Leigh disease. In another embodiment of the invention, including any of the foregoing embodiments, the mitochondrial disorder is Leigh disease with a SURF-1 mutation. In another embodiment of the invention, including any of the foregoing embodiments, the mitochondrial disorder is mitochondrial myopathy, encephalopathy, lactacidosis, and stroke (MELAS). In another embodiment of the invention, including any of the foregoing embodiments, the mitochondrial disorder is Kearns-Sayre Syndrome (KSS). In another embodiment of the invention, the mitochondrial disorder is Myoclonic Epilepsy with Ragged Red Fibers (MERRF). In another embodiment of the invention, the mitochondrial disorder is CoQ10 deficiency. In another embodiment of the invention, including any of the foregoing embodiments, the disorder is Parkinson's disease. In another embodiment of the invention, including any of the foregoing embodiments, the disorder is Huntington's disease. In another embodiment of the invention including any of the foregoing embodiments, the disorder is amyotrophic lateral sclerosis (ALS). In yet another embodiment of the invention including any of the foregoing embodiments, the disorders are cerebral vascular accidents, such as stroke. In another embodiment of the invention including any of the foregoing embodiments, the disorder is hearing impairment. In another embodiment of the invention including any of the foregoing embodiments, the disorder is a pervasive development disorder selected from Autistic Disorder, Asperger's Disorder, Childhood Disintegrative Disorder (CDD), Rett's Disorder, and PDD-Not Otherwise Specified (PDD-NOS).

In another embodiment of the invention, including any of the foregoing embodiments, the compounds described herein are administered to subjects affected with an impaired energy processing disorder due to deprivation, poisoning or toxicity of oxygen.

In another embodiment of the invention, including any of the foregoing embodiments, the compounds described herein are administered to subjects affected with diseases where qualitative and/or quantitative disruptions in the transport of oxygen to tissues result in energy disruption in the function of red cells. Some of these diseases are haemoglobinopathies, such as sickle-cell disease and thalassemia. Another disease is contrast-induced nephropathy or damage due to radiation exposure or injury.

In another embodiment of the invention, including any of the foregoing embodiments, the compounds described herein are administered to subjects suffering from a mitochondrial disorder to modulate one or more of various energy biomarkers, including, but not limited to, lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH(NADH+H$^+$) or NADPH (NADPH+H$^+$) levels; NAD or NADP levels; ATP levels; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), respiratory quotient (VCO2/VO2), and to modulate exercise intolerance (or conversely, modulate exercise tolerance) and to modulate anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In one embodiment, the levels are modulated to a value within about 2 standard deviations of the value in a healthy subject. In another embodiment, the levels are modulated to a value within about 1 standard deviation of the value in a healthy subject. In another embodiment, the levels in a subject are changed by at least about 10% above or below the level in the subject prior to modulation. In another embodiment, the levels are changed by at least about 20% above or below the level in the subject prior to modulation. In another embodiment, the levels are changed by at least about 30% above or below the level in the subject prior to modulation. In another embodiment, the levels are changed by at least about 40% above or below the level in the subject prior to modulation. In another embodiment, the levels are changed by at least about 50% above or below the level in the subject prior to modulation. In another embodiment, the levels are changed by at least about 75% above or below the level in the subject prior to modulation. In another embodiment, the levels are changed by at least about 100% above or at least about 90% below the level in the subject prior to modulation.

In another embodiment, including any of the foregoing embodiments, the subject or subjects in which a method of treating or suppressing a mitochondrial disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

In another embodiment, the invention embraces the use of one or more compounds of formula I, Ia, and/or Ib, in the therapy of mitochondrial disease. In another embodiment, the invention embraces the use of one or more compounds of formula I, Ia, and/or Ib in the manufacture of a medicament for use in therapy of mitochondrial disease.

For all of the compounds and methods described above, the catechol (ortho-hydroquinone) form can also be used in its oxidized (ortho-quinone) form when desired. Likewise, the ortho-quinone form can also be used in its reduced (ortho-hydroquinone, catechol) form when desired.

MODES FOR CARRYING OUT THE INVENTION

The invention embraces compounds of Formula I useful in treating or suppressing mitochondrial disorders, and methods of using such compounds for modulation of energy biomarkers. The compounds of the present invention for treatment or suppression of mitochondrial diseases and associated aspects of the invention are described in more detail herein.

By "subject," "individual," or "patient" is meant an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations. An "effective amount" of a compound embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as a mitochondrial disease, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The invention also includes all stereoisomers of the compounds, including diastereomers and enantiomers. The invention also includes mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York:

Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

Metabolites of the compounds are also embraced by the invention.

"$C_1$-$C_6$ alkyl" is intended to embrace a saturated linear, branched, cyclic, or a combination thereof, hydrocarbon of 1 to 6 carbon atoms. Examples of "$C_1$-$C_6$ alkyl" are methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment, and cyclohexyl.

"Halogen" or "halo" designates fluoro, chloro, bromo, and iodo.

"$C_1$-$C_6$ haloalkyl" is intended to embrace any $C_1$-$C_6$ alkyl substituent having at least one halogen substituent; the halogen can be attached via any valence on the $C_1$-$C_6$ alkyl group. Some examples of $C_1$-$C_6$ haloalkyl is —$CF_3$, —$CCl_3$, —$CHF_2$, —$CHCl_2$, —$CHBr_2$, —$CH_2F$, —$CH_2Cl$.

Diseases Amenable to Treatment or Suppression with Compounds and Methods of the Invention A variety of diseases are believed to be caused or aggravated by mitochondrial disorders and impaired energy processing, and can be treated or suppressed using the compounds and methods of the invention. Such diseases include, but are not limited to, inherited mitochondrial diseases, such as Myoclonic Epilepsy with Ragged Red Fibers (MERRF), Mitochondrial Myopathy, Encephalopathy, Lactacidosis, and Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Leigh disease with a SURF-1 mutation, Kearns-Sayre Syndrome (KSS), Friedreich's Ataxia (FRDA), Alper's disease, POLg-1 disease, diseases with myopathies (including cardiomyopathy and encephalomyopathy), CoQ10 deficiency and renal tubular acidosis; neurodegenerative diseases, such as Parkinson's disease, Alzheimer's disease, amyotrophic lateral sclerosis (ALS, also known as Lou Gehrig's disease), motor neuron diseases; other neurological diseases such as epilepsy; genetic diseases such as Huntington's Disease (which is also a neurological disease); mood disorders such as schizophrenia and bipolar disorder; cerebral vascular accidents such as stroke, and certain age-associated diseases, particularly diseases for which CoQ10 has been proposed for treatment, such as macular degeneration, diabetes, and cancer. Mitochondrial dysfunction is also implicated in excitoxic, neuronal injury, such as that associated with seizures, stroke and ischemia. Mitochondrial dysfunction is also implicated in noise induced, age-induced and ototoxin-induced hearing impairments. Mitochondrial dysfunction is also implicated in certain patients suffering from pervasive development disorders selected from Autistic Disorder, Asperger's Disorder, Childhood Disintegrative Disorder (CDD), Rett's Disorder, and PDD-Not Otherwise Specified (PDD-NOS).

Diseases caused by energy impairment include diseases due to deprivation, poisoning or toxicity of oxygen, and qualitative or quantitative disruption in the transport of oxygen such as haemaglobionopathies, for example thalassemia or sickle cell anemia, contrast induced (CIN) or damage due to radiation exposure or injury.

Oxidative stress is implicated in the exacerbation of several other diseases, such as septic shock, acute respiratory distress syndrome, systemic inflammatory response syndrome, disseminated intravascular coagulation, multiple organ dysfunction, burns, cardiovascular disease, diabetes mellitus, trauma, reperfusion injury, and cancer (see Goodyear-Bruch, C. et al., "Oxidative Stress in Critically Ill Patients" American Journal of Critical Care, 11:543-551 (2002)). Additional information regarding conditions involving oxidative stress is found in the book *Oxidative Stress* (Helmut Sies, ed.), Academic Press: New York, 1991.

Clinical Assessment and Efficacy of Therapy

Several readily measurable clinical markers are used to assess the metabolic state of patients with disorders of the present invention. These markers can also be used as indicators of the efficacy of a given therapy, as the level of a marker is moved from the pathological value to the healthy value. These clinical markers include, but are not limited to, one or more of the previously discussed energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH(NADH+H+) or NADPH (NADPH+H+) levels; NAD or NADP levels; ATP levels; anaerobic threshold; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, MELAS, or KSS, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, MELAS, or KSS is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4): 583-6 (1994)). Changes in the redox state of liver mitochondria can be investigated by measuring the arterial ketone body ratio (acetoacetate/3-hydroxybutyrate:AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements. Monitoring evaluation of redox status in various organs, particularly the brain by imaging are assessed with tracer techniques such as HMPAO, Tc99m-HMPAO, or other used imaging agents. Serum levels of glutathione are assessed in vivo by HMPAO SPECT imaging using Tc99m-HMPAO.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic Acid (Lactate) Levels:

Mitochondrial dysfunction typically results in abnormal levels of lactic acid, as pyruvate levels increase and pyruvate is converted to lactate to maintain capacity for glycolysis. Mitochondrial dysfunction can also result in abnormal levels of $NADH+H^+$, $NADPH+H^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, $NADH(NADH+H^+)$ or $NADPH(NADPH+H^+)$ can be measured by a variety of fluorescent, enzymatic, or electrochemical techniques, e.g., the electrochemical assay described in US 2005/0067303.

Oxygen consumption ($vO_2$ or VO2), carbon dioxide output ($vCO_2$ or VCO2), and respiratory quotient (VCO2/VO2): $vO_2$ is usually measured either while resting (resting $vO_2$) or at maximal exercise intensity ($vO_2$ max). Optimally, both values will be measured. However, for severely disabled patients, measurement of $vO_2$ max may be impractical. Measurement of both forms of $vO_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, Reduced Cytochrome C, and Ratio of Oxidized Cytochrome C to Reduced Cytochrome C:

Cytochrome C parameters, such as oxidized cytochrome C levels ($Cyt\ C_{ox}$), reduced cytochrome C levels ($Cyt\ C_{red}$), and the ratio of oxidized cytochrome C/reduced cytochrome C ratio ($Cyt\ C_{ox}$)/($Cyt\ C_{red}$), can be measured by in vivo near infrared spectroscopy. See, e.g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise Tolerance/Exercise Intolerance:

Exercise intolerance is defined as "the reduced ability to perform activities that involve dynamic movement of large skeletal muscles because of symptoms of dyspnea or fatigue" (Piña et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR(CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable Energy Biomarker | Physical Effect |
|---|---|---|---|
| Respiratory Chain | ↑ NADH | Δ lactate, Δ lactate: pyruvate ratio; and Δ acetoacetate: β-hydroxy butyrate ratio | Metabolic dyscrasia & fatigue |
| Respiratory Chain | ↓ H$^+$ gradient | Δ ATP | Organ dependent dysfunction |
| Respiratory Chain | ↓ Electron flux | Δ VO$_2$, RQ, BMR, ΔT, AT, pH | Metabolic dyscrasia & fatigue |
| Mitochondria & cytosol | ↓ ATP, ↓ VO$_2$ | Δ Work, ΔHR (CO) | Exercise intolerance |
| Mitochondria & cytosol | ↓ ATP | Δ PCr | Exercise intolerance |
| Respiratory Chain | ↓ Cyt C$_{Ox/Red}$ | Δ λ~700-900 nM (Near Infrared Spectroscopy) | Exercise intolerance |
| Intermediary metabolism | ↓ Catabolism | Δ C$^{14}$-Labeled substrates | Metabolic dyscrasia & fatigue |
| Respiratory Chain | ↓ Electron Flux | Δ Mixed Venous VO$_2$ | Metabolic dyscrasia & fatigue |

TABLE 1-continued

| Site of Dysfunction | Biochemical Event | Measurable Energy Biomarker | Physical Effect |
|---|---|---|---|
| Mitochondria & cytosol | ↑ Oxidative stress | Δ Tocopherol & Tocotrienols, CoQ10, docosahexanoic acid | Uncertain |
| Mitochondria & cytosol | ↑ Oxidative stress | Δ Glutahione$_{red}$ | Uncertain |
| Mitochondria & cytosol | Nucleic acid oxidation | ≡ 8-hydroxy 2-deoxy guanosine | Uncertain |
| Mitochondria & cytosol | Lipid oxidation | Δ Isoprostane (s), eicasanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by a mitochondrial disease in accordance with the methods of the invention may result in the inducement of a reduction or alleviation of symptoms in the subject, e.g., to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one or any combination of the energy biomarkers described herein provides conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

In addition to the methods described herein, the level of oxidative stress in a subject, and the response of a subject to therapy to alleviate oxidative stress, can be measured by other techniques known in the art, such as those disclosed in "Oxidation of Biological Systems: Oxidative Stress Phenomena, Antioxidants, Redox Reactions, and Methods for Their Quantification" by Ron Kohen and Abraham Nyska, Toxicologic Pathology, 30(6):620-650 (2002), and more specifically in the section entitled "Methods For Determination Of ROS And Radicals" at pages 633-635 ("ROS" is an abbreviation for "Reactive Oxygen Species"). This disclosure is hereby incorporated by reference herein.

Use of Compounds for Modulation of Energy Biomarkers

In addition to monitoring energy biomarkers to assess the status of treatment or suppression of mitochondrial diseases, the compounds of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with a mitochondrial disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds of the invention can also be used in research applications. They can be used in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds of formula I, Ia, and Ib, can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject in which modulation of one or more energy biomarkers can be assayed; 2) administering one or more compounds of the invention to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds of the invention to the cell sample or tissue sample; 3) determining the amount of modulation of the one or more energy biomarkers after administration of the at least two compounds, compared to the status of the energy biomarker prior to administration of the at least compounds, and 4) selecting a compound for use in treatment, suppression, or modulation based on the amount of modulation determined in step 3).

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

The invention also provides articles of manufacture and kits containing materials useful for treating or suppressing mitochondrial diseases. The invention also provides kits comprising any one or more of the compounds of formulas I, Ia, and Ib. In some embodiments, the kit of the invention comprises the container described above.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are an effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, they can also be used in combination with one or more other agents used in the treatment or suppression of disorders. Representative agents useful in combination with the compounds of the invention for the treatment or suppression of mitochondrial diseases include, but are not limited to, Coenzyme Q, vitamin E, alpha-tocopherol quinone, alpha-tocotrienol quinone, idebenone, MitoQ, vitamins, and antioxidant compounds.

When additional active agents are used in combination with the compounds of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following nonlimiting examples.

In general, the nomenclature used in this application was generated with the help of naming package within the ChemOffice™ version 11.0 suite of programs by CambridgeSoft Corp (Cambridge, Mass.).

Preparation of Compounds of the Invention

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Brief Description of Reaction Schemes

Reaction Scheme 1 below illustrates the synthesis of compounds of Formula Ia, where $R^4$ and $R^5$ together with the atoms to which they are attached form a double bond.

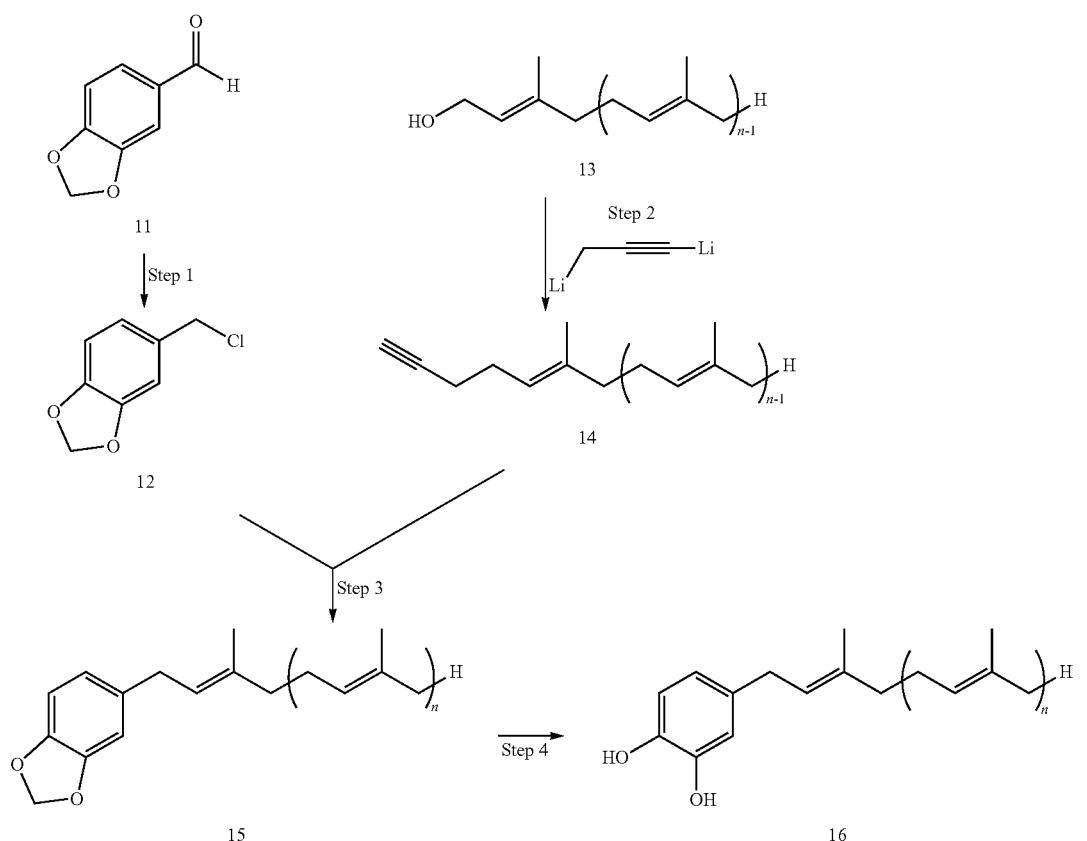

In Reaction Scheme 1, Step 1, the commercially available piperonyl aldehyde (11) (CAS 120-57-0) is reduced to the alcohol by treatment with a hydride reducing agent such as sodium borohydride, and converted tho the chlor methylated aromatic compound (12) by treatment of the boronate aduct with concentrated hydrochloric acid.

In Step 2, compound (13) (for example all trans farnesol (n−1=2) (CAS 4602-84-0), may be converted to the allylic farnesyl chloride by treatment with $PCl_3$, DMF complex and the resultant allylic chloride displaced with dilithiated propyne to generate the terminal alkyne (14). In Step 3, treatment of the alykyne (14) with $AlMe_3$ in the presence of $Cp_2ZrCl_2$ in a chlorinated solvent to give the reactive aluminum-alkene complex which is then treated with the chloromethylated protected catechol (4) in the presence of a Nickel(0) or Palladium(0) catalyst in an appropriate ethereal solvent, will give the protected compound of formula (15). Deprotection of the catechol may then be performed by $AlBr_3$ in EtSH to give the catechol (16).

Reaction Scheme 2 below illustrates the synthesis of compounds of Formula Ia, where $R^4$ is OH and $R^5$ is hydrogen.

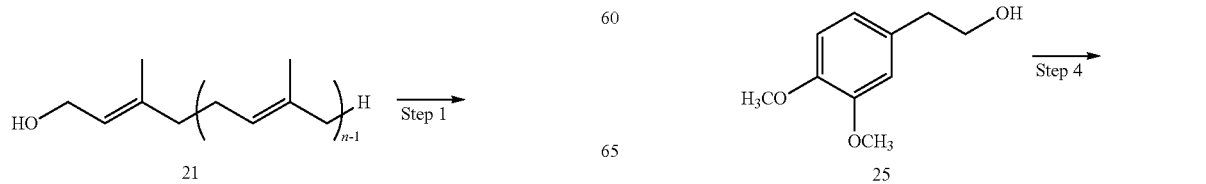

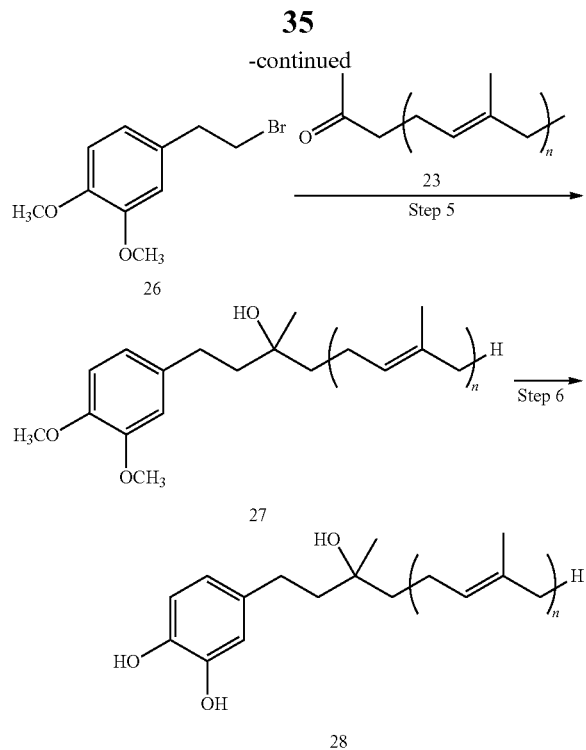

In Reaction Scheme 2, Step 1, compound (21) (for example farnesol) is converted to the allylic chloride (22) by treatment with PCl₃ in DMF and the resulting chloride is treated in Step 2 with the enolate of acetone to generate compound 23 (for example farnesyl acetone).

In Step 3, the phenols of compound 25 (Eugenol CAS#95-53-0) are protected as methoxy groups by treating with dimethyl sulfite in the presence of NaOH and the terminal is clipped to an aldehyde via a Ruthenium catalyzed sodium periodate oxidation sequence, followed by a reduction to a primary alcohol with sodium borohydride giving alcohol (25), which is converted in step 4 to the bromide (26) with CBr₄.

In step 5, addition of magnesium turnings to alkyl bromide (26) in an ethereal solvent generates a reactive Grignard reagent which is treated with farnesyl acetone (23) to generate the requisite tertiary alcohol (27). Deprotection of the phenols may be achieved by treatment with AlBr₃ and EtSH or BBr₃ in CH₂Cl₂ to reveal the desired catechol derivative (28).

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol ("MeOH"), acetone, water, acetonitrile, 1,4-dioxane, dimethylformamide ("DMF"), benzene, toluene, xylene, tetrahydrofuran ("THF"), chloroform, methylene chloride (or dichloromethane, ("DCM")), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

$^1$H and $^{13}$C NMR were obtained on a Varian Ultrashielded magnet at 400 MHz and 100 MHz respectively in deutrated solvents as noted. All spectra are referenced in ppm to either their residual solvent peak, as defined in Gottlieb, H. E. et. al; *J. Org. Chem.* 1997, 62, 7512-7515, or TMS at 0.00 ppm. The FIDs were processed using Varian VNMRJ software or ACD Version 11 1D NMR processor. JR spectra were obtained on a Perkin ELMER Spectrum 100 equipped with a LiTa detector using a PE Universal single bounce SeGe/Diamond ATR stage as neat samples. Melting points were obtained on an Optimelt MPA-100 in unsealed borosilicate glass tubes at 5° C./min. HPLC and HPLC/MS data were obtained on an Agilent 1100 LC system attached to both a Diode Array spectrophotometer (see below) and a HP 1956B mass using an Agilent ACPI/ES multimode source in mixed mode. The HPLC column was a Phenomenex Luna phenyl-hexyl 150 mm×4.6 mm 5 μm silica supported column eluting with water/acetonitrile containing 0.02% (v/v) formic acid. Spectra were processed with Agilent chemstation software. Chromatographic separation was carried out on a Teledyne-ISCO Combiflash Companion using ISCO Redisep pre-packaged columns.

The starting compounds, e.g., eugenol, farnesol and piperonyl aldehyde are commercially available, e.g. from Aldrich Chemical Company, Milwaukee, Wis. Or at www.signaaldrich.com, or may be readily prepared by those skilled in the art using commonly employed methodology.

BIOLOGICAL EXAMPLES

Example A

Screening Compounds of the Invention in Human Dermal Fibroblasts from Friedreich's Ataxia Patients An initial screen was performed to identify compounds effective for the amelioration of redox disorders. Test samples, 4 reference compounds (idebenone, decylubiquinone, Trolox and α-tocopherol acetate), and solvent controls were tested for their ability to rescue FRDA fibroblasts stressed by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24):3055 (2002)). This specific BSO-mediated cell death can be prevented by administration of antioxidants or molecules involved in the antioxidant pathway, such as α-tocopherol, selenium, or small molecule glutathione peroxidase mimetics. However, antioxidants differ in their potency, i.e. the concentration at which they are able to rescue BSO-stressed FRDA fibroblasts.

MEM (a medium enriched in amino acids and vitamins, catalog no. 1-31F24-I) and Medium 199 (M199, catalog no. 1-21F22-I) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, (+)-α-tocopherol acetate, decylubiquinone, and insulin from bovine pancreas were purchased from Sigma. Trolox (6-Hydroxy-2,5,7,8-tetramethylchromane-2-carboxylic acid) was obtained from Fluka. Idebenone was obtained from Chemo Iberica. Calcein AM was purchased from Molecular Probes. Cell culture medium was made by combining 125 ml M199 EBS, 50 ml Fetal Calf Serum, 100 U/ml penicillin, 100 µg/ml streptomycin, 2 mM glutamine, 10 µg/ml insulin, 10 ng/ml EGF, and 10 ng/ml bFGF; MEM EBS was added to make the volume up to 500 ml. A 10 mM BSO solution was prepared by dissolving 444 mg BSO in 200 ml of medium (Invitrogen, Carlsbad, Calif.) with subsequent filter-sterilization. During the course of the experiments, this solution was stored at +4° C. The cells were obtained from the Coriell Cell Repositories (Camden, N.J.; repository number GM04078) and grown in 10 cm tissue culture plates. Every third day, they were split at a 1:3 ratio.

The test samples are supplied in 1.5 ml glass vials. The compounds are diluted with DMSO, ethanol or PBS to result in a 5 mM stock solution. Once dissolved, they are stored at −20° C. Reference antioxidants (idebenone, decylubiquinone, α-tocopherol acetate and trolox) are dissolved in DMSO.

Test samples are screened according to the following protocol: A culture with FRDA fibroblasts is started from a 1 ml vial with approximately 500,000 cells stored in liquid nitrogen. Cells are propagated in 10 cm cell culture dishes by splitting every third day in a ratio of 1:3 until nine plates are available. Once confluent, fibroblasts are harvested. For 54 micro titer plates (96 well-MTP) a total of 14.3 million cells (passage eight) are re-suspended in 480 ml medium, corresponding to 100 µl medium with 3,000 cells/well. The remaining cells are distributed in 10 cm cell culture plates (500,000 cells/plate) for propagation. The plates are incubated overnight at 37° C. in a atmosphere with 95% humidity and 5% $CO_2$ to allow attachment of the cells to the culture plate.

MTP medium (243 µl) is added to a well of the microtiter plate. The test compounds are unfrozen, and 7.5 µl of a 5 mM stock solution is dissolved in the well containing 243 µl medium, resulting in a 150 µM master solution. Serial dilutions from the master solution were made. The period between the single dilution steps is kept as short as possible (generally less than 1 second).

Plates are kept overnight in the cell culture incubator. The next day, 10 µl of a 10 mM BSO solution are added to the wells, resulting in a 1 mM final BSO concentration. Forty-eight hours later, three plates were examined under a phase-contrast microscope to verify that the cells in the 0% control (wells E1-H1) are clearly dead. The medium from all plates is discarded, and the remaining liquid is removed by gently tapping the plate inversed onto a paper towel.

100 µl of PBS containing 1.2 µM Calcein AM are then added to each well. The plates are incubated for 50-70 minutes at room temperature. After that time the PBS is discarded, the plate gently tapped on a paper towel and fluorescence (excitation/emission wavelengths of 485 nm and 525 nm, respectively) is read on a Gemini fluorescence reader. Data is imported into Microsoft Excel (EXCEL is a registered trademark of Microsoft Corporation for a spreadsheet program) and used to calculate the $EC_{50}$ concentration for each compound.

The compounds are tested three times, i.e., the experiment is performed three times, the passage number of the cells increasing by one with every repetition.

The solvents (DMSO, ethanol, PBS) neither have a detrimental effect on the viability of non-BSO treated cells nor did they have a beneficial influence on BSO-treated fibroblasts even at the highest concentration tested (1%). None of the compounds show auto-fluorescence. The viability of non-BSO treated fibroblasts is set as 100%, and the viability of the BSO- and compound-treated cells is calculated as relative to this value.

Compounds of the present invention are considered active if they exhibit protection against FRDA with an $EC_{50}$ of less than about 500 nM.

Example B

Screening Compounds of the Invention in Fibroblasts from Huntington's Patients

Compounds of the invention are tested using a screen similar to the one described in Example A, but substituting FRDA cells with Huntington's cells obtained from the Coriell Cell Repositories (Camden, N.J.; repository number GM 04281). The compounds are tested for their ability to rescue human dermal fibroblasts from Huntington's patients from oxidative stress.

Compounds of the present invention are considered active if they exhibit protection against Huntington's with an $EC_{50}$ of less than about 500 nM.

Example C

Screening Compounds of the Invention in Fibroblasts from Leber's Hereditary Optic Neuropathy Patients Compounds of the invention are tested using a screen similar to the one described in Example A, but substituting FRDA cells with Leber's Hereditary Optic Neuropathy (LHON) cells obtained from the Coriell Cell Repositories (Camden, N.J.; repository number GM03858). The compounds are tested for their ability to rescue human dermal fibroblasts from LHON patients from oxidative stress.

Compounds of the present invention are considered active if they exhibit protection against LHON with an $EC_{50}$ of less than about 500 nM.

Example D

Screening Compounds of the Invention in Fibroblasts from Parkinson's Disease Patients Compounds of the invention are tested using a screen similar to the one described in Example A described in Example A, but substituting FRDA cells with Parkinson's Disease (PD) cells obtained from the Coriell Cell Repositories (Camden, N.J.; repository number AG20439). The compounds are tested for their ability to rescue human dermal fibroblasts from Parkinson's disease patients from oxidative stress.

Compounds of the present invention are considered active if they exhibit protection against Parkinson's with an $EC_{50}$ of less than about 500 nM.

Example E

Screening Compounds of the Invention in Fibroblasts from CoQ10 Deficient Patients Compounds of the invention are tested using a screen similar to the one described in Example A, but substituting FRDA cells with cells obtained from CoQ10 deficient patients harboring a CoQ2 mutation. The compounds are tested for their ability to rescue human dermal fibroblasts from CoQ10 deficient patients from oxidative stress.

Compounds of the present invention are considered active if they exhibit protection against CoQ10 deficiency with an $EC_{50}$ of less than about 500 nM.

Example F

In Vitro System for Drug Ototoxicity Screening

The conditionally immortalized auditory HEI-OC1 cell line from long-term cultures of transgenic mice Immortomouse™ cochleas has been described in Kalinec, G. et al., *Audiol. Nerootol.* 2003; 8, 177-189/. It provides a powerful tool for the in vitro study of auditory cells. These cells are more sensitive to aminoglycoside-induced apoptosis that cells from fibroblastic origin. As described in So, H. S., *Hearing Research* (2005) 204, 127-139 and in Devarajan et al., *Hearing Research* (2002), 174 45-54, HEI-OC1 cells are maintained in high glucose Dulbecco's modified Eagle medium (DMEM) containing 10% FBS under permissive conditions, 33° C., 10% $CO_2$. Cells are incubated with varying concentrations of platinum-containing antineoplastic agents, such as cisplatin and its analogs or aminoglycoside antibiotics such as gentamicin and its analogs, for different time periods. Cells incubated in diluent alone are the controls.

Example G

Screening Compounds of the Invention in Human Dermal Fibroblasts from Autistic Patients A screen is performed to identify compounds effective for the amelioration of ASD. Test samples, and solvent controls are tested for their ability to rescue ASD fibroblasts stressed by addition of L-buthionine-(S,R)-sulfoximine (BSO). MEM (a medium enriched in amino acids and vitamins, catalog no. Gibco 11965) and Fetal Calf Serum are obtained from Invitrogen. Basic fibroblast growth factor and epidermal growth factor are purchased from PeproTech. Penicillin-streptomycin-glutamine mix, L-buthionine (S,R)-sulfoximine, and insulin from bovine pancreas are purchased from Sigma. Calcein AM is purchased from Molecular Probes. Cell culture medium (ATP) is made by combining 75 ml Fetal Calf Serum, 100 U/ml penicillin, 100 µg/ml streptomycin, 2 mM glutamine, 10 ng/ml EGF, and 10 ng/ml bFGF; MEM EBS is added to make the volume up to 500 ml. A 10 mM BSO solution is prepared by dissolving 444 mg BSO in 200 ml of medium with subsequent filter-sterilization. During the course of the experiments, this solution is stored at +4° C. The cells obtained from Dr. J. M. Shoffner, Medical Neurogenetics, Atlanta, Ga. are grown in 10 cm tissue culture plates. Every week, they are split at a 1:3 ratio.

The samples are supplied in 1.5 ml glass vials. The compounds are diluted with DMSO, ethanol or PBS to result in a 5 mM stock solution. Once dissolved, they are stored at −20° C.

The samples are screened according to the following protocol:

A culture with ASD fibroblasts is started from a 1 ml vial with approximately 500,000 cells stored in liquid nitrogen. Cells are propagated in 10 cm cell culture dishes by splitting every week in a ratio of 1:3 until nine plates are available. Once confluent, fibroblasts are harvested. For 54 micro titer plates (96 well-MTP) a total of 14.3 million cells (passage eight) are re-suspended in 480 ml medium, corresponding to 100 µl medium with 3,000 cells/well. The remaining cells are distributed in 10 cm cell culture plates (500,000 cells/plate) for propagation. The plates are incubated overnight at 37° C. in an atmosphere with 95% humidity and 5% $CO_2$ to allow attachment of the cells to the culture plate.

MTP medium (243 µl) is added to a well of the microtiter plate. The test compounds are unfrozen, and 7.5 µl of a 5 mM stock solution is dissolved in the well containing 243 µl medium, resulting in a 150 µM master solution. Serial dilutions from the master solution are made. The period between the single dilution steps is kept as short as possible (generally less than 1 second).

Plates are kept overnight in the cell culture incubator. The next day, 10 µl of a 10 mM BSO solution are added to the wells, resulting in a 1 mM final BSO concentration. Forty-eight hours later, three plates are examined under a phase-contrast microscope to verify that the cells in the 0% control (wells E1-H1) are clearly dead. The medium from all plates is discarded, and the remaining liquid is removed by gently tapping the plate inversed onto a paper towel.

100 µl of PBS containing 1.2 µM Calcein AM are then added to each well. The plates are incubated for 50-70 minutes at room temperature. After that time the PBS is discarded, the plate gently tapped on a paper towel and fluorescence (excitation/emission wavelengths of 485 nm and 525 nm, respectively) is read on a Gemini fluorescence reader. Data was imported into Microsoft Excel® and used to calculate the $EC_{50}$ concentration for each compound.

The compounds are tested three times, i.e., the experiment is performed three times, the passage number of the cells increasing by one with every repetition.

The solvents (DMSO, ethanol, PBS) neither have a detrimental effect on the viability of non-BSO treated cells nor do they have a beneficial influence on BSO-treated fibroblasts even at the highest concentration tested (1%). None of the compounds show auto-fluorescence. The viability of non-BSO treated fibroblasts is set as 100%, and the viability of the BSO- and compound-treated cells is calculated as relative to this value.

Certain compounds of the present invention are considered to be active if they exhibit protection against ASD with an $EC_{50}$ of less than 500 nM.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of Formula I:

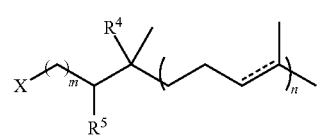

Formula I where X is selected from the group consisting of:

(A)

[structure with R¹, R², R³, R⁶O, OR⁶ on benzene ring with *]

(B)

[quinone structure with R¹, R², R³ and *]

(C)

[structure with R¹, R², R³, R⁶O, OR⁶ on benzene ring with *]

(D)

[quinone structure with R¹, R², R³ and *]

where the * indicates the point of attachment of X to the rest of the molecule;
each bond indicated by a dashed line is independently double or single;
m is 0 or 1;
n is 1 to 10;
$R^1$, $R^2$ and $R^3$ are independently selected from the group consisting of hydrogen, $C_1$-$C_6$-alkyl, $C_1$-$C_6$-haloalkyl, and halogen;
$R^4$ is OH and $R^5$ is hydrogen; or $R^4$ and $R^5$ are both hydrogen; and
$R^6$ is hydrogen, $C_1$-$C_6$-alkyl, —C(O)$C_1$-$C_6$-alkyl or —C(O)aryl;
or a salt, a stereoisomer, a mixture of stereoisomers, a solvate or a hydrate thereof.

2. The compound of claim 1, having the formula Ia:

Formula Ia

[structure showing R¹, R², R³, R⁴, R⁵, HO, OH with m and n]

where,
each bond indicated by a dashed line is independently double or single;
m is 0 or 1;
n is 1 to 4;
$R^1$, $R^2$ and $R^3$ are independently selected from the group consisting of hydrogen, $C_1$-$C_6$-alkyl, $C_1$-$C_6$-haloalkyl, and halogen;
$R^4$ is OH and $R^5$ is hydrogen; or $R^4$ and $R^5$ are both hydrogen;
or a salt, a stereoisomer, a mixture of stereoisomers, a solvate or a hydrate thereof.

3. The compound of claim 1, having the Formula Ib:

Formula Ib

[structure showing R¹, R², R³, R⁴, R⁵, OH, OH with m and n]

where,
each bond indicated by a dashed line is independently double or single;
m is 0 or 1;
n is 1 to 4;
$R^1$, $R^2$ and $R^3$ are independently selected from the group consisting of hydrogen, $C_1$-$C_6$-alkyl, $C_1$-$C_6$-haloalkyl, and halogen;
$R^4$ is OH and $R^5$ is hydrogen; or $R^4$ and $R^5$ are both hydrogen;
or a salt, a stereoisomer, a mixture of stereoisomers, a solvate or a hydrate thereof.

4. The compound of claim 1, where m is 1 and n is 1-4.
5. The compound of claim 1, where m is 0 and n is 1-4.
6. The compound of claim 1, where $R^4$ and $R^5$ are both hydrogen.
7. The compound of claim 1, where $R^4$ is OH and $R^5$ is hydrogen.
8. A pharmaceutical composition comprising the compound of claim 1 and a pharmaceutically acceptable excipient.
9. The compound of claim 1, wherein the compound is selected from the group consisting of:
4-(3-hydroxy-3,7,11,15-tetramethylhexadeca-6,10,14-trien-1-yl)benzene-1,2-diol;
4-(3-hydroxy-3,7,11,15,19-pentamethylicosa-6,10,14,18-tetraen-1-yl)benzene-1,2-diol;
4-(3-hydroxy-3,7,11-trimethyldodeca-6,10-dien-1-yl)benzene-1,2-diol;
4-(3-hydroxy-3,7-dimethyloct-6-en-1-yl)benzene-1,2-diol;
4-(3-hydroxy-3,7,11,15-tetramethylhexadeca-6,10,14-trien-1-yl)-3,5,6-trimethylbenzene-1,2-diol;
4-(3-hydroxy-3,7,11,15-tetramethylhexadeca-6,10,14-trien-1-yl)-3,5-dimethylbenzene-1,2-diol;
5-(3-hydroxy-3,7,11,15-tetramethylhexadeca-6,10,14-trien-1-yl)-3,4-dimethylbenzene-1,2-diol;
4-(3-hydroxy-3,7,11,15-tetramethylhexadeca-6,10,14-trien-1-yl)-3,6-dimethylbenzene-1,2-diol;
5-(3-hydroxy-3,7,11,15-tetramethylhexadeca-6,10,14-trien-1-yl)-3-methylbenzene-1,2-diol;

4-(3-hydroxy-3,7,11,15-tetramethylhexadeca-6,10,14-trien-1-yl)-5-methylbenzene-1,2-diol;
4-(3-hydroxy-3,7,11,15-tetramethylhexadeca-6,10,14-trien-1-yl)-3-methylbenzene-1,2-diol;
4-(3-hydroxy-3,7,11,15-tetramethylhexadecyl)benzene-1,2-diol;
4-(3-hydroxy-3,7,11,15-tetramethylhexadecyl)-3,5,6-trimethylbenzene-1,2-diol;
4-(3-hydroxy-3,7,11,15-tetramethylhexadecyl)-3,5-dimethylbenzene-1,2-diol;
5-(3-hydroxy-3,7,11,15-tetramethylhexadecyl)-3,4-dimethylbenzene-1,2-diol;
4-(3-hydroxy-3,7,11,15-tetramethylhexadecyl)-3,6-dimethylbenzene-1,2-diol;
5-(3-hydroxy-3,7,11,15-tetramethylhexadecyl)-3-methylbenzene-1,2-diol;
4-(3-hydroxy-3,7,11,15-tetramethylhexadecyl)-5-methylbenzene-1,2-diol;
4-(3-hydroxy-3,7,11,15-tetramethylhexadecyl)-3-methylbenzene-1,2-diol;
4-(3,7,11,15-tetramethylhexadecyl)benzene-1,2-diol;
3,4,6-trimethyl-5-(3,7,11,15-tetramethylhexadecyl)benzene-1,2-diol;
3,4-dimethyl-5-(3,7,11,15-tetramethylhexadecyl)benzene-1,2-diol;
3,6-dimethyl-4-(3,7,11,15-tetramethylhexadecyl)benzene-1,2-diol;
3,5-dimethyl-4-(3,7,11,15-tetramethylhexadecyl)benzene-1,2-diol;
4-methyl-5-(3,7,11,15-tetramethylhexadecyl)benzene-1,2-diol;
3-methyl-5-(3,7,11,15-tetramethylhexadecyl)benzene-1,2-diol;
3-methyl-4-(3,7,11,15-tetramethylhexadecyl)benzene-1,2-diol;
3-(3-hydroxy-3,7,11,15-tetramethylhexadeca-6,10,14-trien-1-yl)benzene-1,2-diol;
3-(3-hydroxy-3,7,11,15-tetramethylhexadeca-6,10,14-trien-1-yl)-4,5,6-trimethylbenzene-1,2-diol;
6-(3-hydroxy-3,7,11,15-tetramethylhexadeca-6,10,14-trien-1-yl)-3,4-dimethylbenzene-1,2-diol;
3-(3-hydroxy-3,7,11,15-tetramethylhexadeca-6,10,14-trien-1-yl)-4,5-dimethylbenzene-1,2-diol;
3-(3-hydroxy-3,7,11,15-tetramethylhexadeca-6,10,14-trien-1-yl)-4,6-dimethylbenzene-1,2-diol;
3-(3-hydroxy-3,7,11,15-tetramethylhexadeca-6,10,14-trien-1-yl)-4-methylbenzene-1,2-diol;
3-(3-hydroxy-3,7,11,15-tetramethylhexadeca-6,10,14-trien-1-yl)-5-methylbenzene-1,2-diol;
3-(3-hydroxy-3,7,11,15-tetramethylhexadeca-6,10,14-trien-1-yl)-6-methylbenzene-1,2-diol;
3-(3-hydroxy-3,7,11,15,19-pentamethylicosa-6,10,14,18-tetraen-1-yl)benzene-1,2-diol;
3-(3-hydroxy-3,7,11-trimethyldodeca-6,10-dien-1-yl)benzene-1,2-diol; and
3-(3-hydroxy-3,7-dimethyloct-6-en-1-yl)benzene-1,2-diol;
or a stereoisomer, mixture of stereoisomers, solvate, or hydrate thereof.

10. The compound of claim 1, wherein the compound is selected from the group consisting of: 4-(6E,10E)-3-hydroxy-3,7,11,15-tetramethylhexadeca-6,10,14-trien-1-yl)benzene-1,2-diol; and 3-((6E,10E)-3-hydroxy-3,7,11,15-tetramethylhexadeca-6,10,14-trien-1-yl)benzene-1,2-diol.

* * * * *

UNITED STATES PATENT AND TRADEMARK OFFICE
CERTIFICATE OF CORRECTION

PATENT NO. : 9,464,016 B2  Page 1 of 1
APPLICATION NO. : 14/124671
DATED : October 11, 2016
INVENTOR(S) : Mollard et al.

It is certified that error appears in the above-identified patent and that said Letters Patent is hereby corrected as shown below:

In the Claims

Column 41, Lines 58-65, Claim 2, the chemical structure of Formula Ia should read:

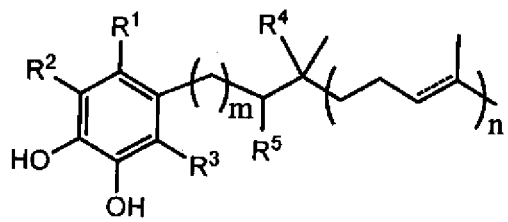

Signed and Sealed this
Third Day of January, 2017

Michelle K. Lee
*Director of the United States Patent and Trademark Office*